United States Patent
Corvari et al.

(10) Patent No.: US 9,376,491 B2
(45) Date of Patent: Jun. 28, 2016

(54) IL-17 ANTIBODY FORMULATION AND METHOD OF TREATMENT USING SAME

(71) Applicant: Eli Lilly and Company, Indianapolis, IN (US)

(72) Inventors: Vincent John Corvari, Carmel, IN (US); Barbara Ann Williams, Indianapolis, IN (US); Patrick Daniel Donovan, Zionsville, IN (US); Aaron Paul Markham, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 14/379,755

(22) PCT Filed: Mar. 1, 2013

(86) PCT No.: PCT/US2013/028516
§ 371 (c)(1),
(2) Date: Aug. 20, 2014

(87) PCT Pub. No.: WO2013/134052
PCT Pub. Date: Sep. 12, 2013

(65) Prior Publication Data
US 2015/0010573 A1     Jan. 8, 2015

Related U.S. Application Data

(60) Provisional application No. 61/607,671, filed on Mar. 7, 2012.

(51) Int. Cl.
*A61K 39/395* (2006.01)
*C07K 16/24* (2006.01)
*A61K 39/00* (2006.01)

(52) U.S. Cl.
CPC ......... *C07K 16/244* (2013.01); *A61K 39/39591* (2013.01); *A61K 2039/505* (2013.01); *C07K 2317/50* (2013.01)

(58) Field of Classification Search
None
See application file for complete search history.

(56) References Cited

FOREIGN PATENT DOCUMENTS

| WO | 2007070750 | 6/2007 |
| WO | 2008068246 | 6/2008 |

OTHER PUBLICATIONS

He, F., et al., "Screening of Monoclonal Antibody Formulations based on High-Throughput Thermostability and Viscosity Measurements: Design of Experiment and Statistical Analysis," Journal of Pharmaceutical Sciences, 2011 vol. 100, No. 4, Apr. 2011, pp. 1330-1340.

*Primary Examiner* — Dong Jiang
(74) *Attorney, Agent, or Firm* — Gregory A. Cox

(57) ABSTRACT

The present invention provides stabilized pharmaceutical formulations for anti-IL-17 antibodies, comprising e.g. citrate, sodium chloride and polysorbate-80 at pH 5.7. These stabilized anti-IL-17 antibody pharmaceutical formulations can be used to treat rheumatoid arthritis, psoriasis, ankylosing spondilitis, psoriatic arthritis or multiple myeloma.

8 Claims, No Drawings

SEQUENCE LISTING

<160> NUMBER OF SEQ ID NOS: 5

<210> SEQ ID NO 1
<211> LENGTH: 155
<212> TYPE: PRT
<213> ORGANISM: Homo sapiens

<400> SEQUENCE: 1

Met Thr Pro Gly Lys Thr Ser Leu Val Ser Leu Leu Leu Leu Leu Ser
1               5                   10                  15

```
Leu Glu Ala Ile Val Lys Ala Gly Ile Thr Ile Pro Arg Asn Pro Gly
            20                  25                  30

Cys Pro Asn Ser Glu Asp Lys Asn Phe Pro Arg Thr Val Met Val Asn
        35                  40                  45

Leu Asn Ile His Asn Arg Asn Thr Asn Thr Asn Pro Lys Arg Ser Ser
50                  55                  60

Asp Tyr Tyr Asn Arg Ser Thr Ser Pro Trp Asn Leu His Arg Asn Glu
65                  70                  75                  80

Asp Pro Glu Arg Tyr Pro Ser Val Ile Trp Glu Ala Lys Cys Arg His
                85                  90                  95

Leu Gly Cys Ile Asn Ala Asp Gly Asn Val Asp Tyr His Met Asn Ser
            100                 105                 110

Val Pro Ile Gln Gln Glu Ile Leu Val Leu Arg Arg Glu Pro Pro His
        115                 120                 125

Cys Pro Asn Ser Phe Arg Leu Glu Lys Ile Leu Val Ser Val Gly Cys
    130                 135                 140

Thr Cys Val Thr Pro Ile Val His His Val Ala
145                 150                 155

<210> SEQ ID NO 2
<211> LENGTH: 112
<212> TYPE: PRT
<213> ORGANISM: Artificial Sequence
<220> FEATURE:
<223> OTHER INFORMATION: synthetic construct

<400> SEQUENCE: 2

Asp Ile Val Met Thr Gln Thr Pro Leu Ser Leu Ser Val Thr Pro Gly
1               5                   10                  15

Gln Pro Ala Ser Ile Ser Cys Arg Ser Ser Arg Ser Leu Val His Ser
            20                  25                  30

Arg Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ile Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Leu Pro Phe Thr Phe Gly Gln Gly Thr Lys Leu Glu Ile Lys
            100                 105                 110

<210> SEQ ID NO 3
<211> LENGTH: 119
<212> TYPE: PRT
<213> ORGANISM: Artificial Sequence
<220> FEATURE:
<223> OTHER INFORMATION: synthetic construct

<400> SEQUENCE: 3

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

His Ile His Trp Val Arg Gln Ala Pro Gly Gln Gly Leu Glu Trp Met
        35                  40                  45

Gly Val Ile Asn Pro Met Tyr Gly Thr Thr Asp Tyr Asn Gln Arg Phe
    50                  55                  60
```

```
Lys Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Tyr Asp Tyr Phe Thr Gly Thr Gly Val Tyr Trp Gly Gln Gly
            100                 105                 110

Thr Leu Val Thr Val Ser Ser
        115

<210> SEQ ID NO 4
<211> LENGTH: 219
<212> TYPE: PRT
<213> ORGANISM: Artificial Sequence
<220> FEATURE:
<223> OTHER INFORMATION: synthetic construct

<400> SEQUENCE: 4

Asp Ile Val Met Thr Gln Thr Pro Leu Ser Leu Ser Val Thr Pro Gly
  1               5                  10                  15

Gln Pro Ala Ser Ile Ser Cys Arg Ser Ser Arg Ser Leu Val His Ser
             20                  25                  30

Arg Gly Asn Thr Tyr Leu His Trp Tyr Leu Gln Lys Pro Gly Gln Ser
         35                  40                  45

Pro Gln Leu Leu Ile Tyr Lys Val Ser Asn Arg Phe Ile Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                 85                  90                  95

Thr His Leu Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 5
<211> LENGTH: 445
<212> TYPE: PRT
<213> ORGANISM: Artificial Sequence
<220> FEATURE:
<223> OTHER INFORMATION: synthetic construct

<400> SEQUENCE: 5

Gln Val Gln Leu Val Gln Ser Gly Ala Glu Val Lys Lys Pro Gly Ser
  1               5                  10                  15

Ser Val Lys Val Ser Cys Lys Ala Ser Gly Tyr Ser Phe Thr Asp Tyr
```

```
            20                  25                  30
His Ile His Trp Val Arg Gln Ala Pro Gly Gln Gly Leu Glu Trp Met
            35                  40                  45
Gly Val Ile Asn Pro Met Tyr Gly Thr Thr Asp Tyr Asn Gln Arg Phe
         50                  55                  60
Lys Gly Arg Val Thr Ile Thr Ala Asp Glu Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Tyr Asp Tyr Phe Thr Gly Thr Gly Val Tyr Trp Gly Gln Gly
            100                 105                 110
Thr Leu Val Thr Val Ser Ser Ala Ser Thr Lys Gly Pro Ser Val Phe
            115                 120                 125
Pro Leu Ala Pro Cys Ser Arg Ser Thr Ser Glu Ser Thr Ala Ala Leu
            130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Lys Thr Tyr Thr Cys Asn Val Asp His Lys Pro
            195                 200                 205
Ser Asn Thr Lys Val Asp Lys Arg Val Glu Ser Lys Tyr Gly Pro Pro
            210                 215                 220
Cys Pro Pro Cys Pro Ala Pro Glu Phe Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser Gln Glu Asp Pro Glu Val
            260                 265                 270
Gln Phe Asn Trp Tyr Val Asp Gly Val Glu Val His Asn Ala Lys Thr
            275                 280                 285
Lys Pro Arg Glu Glu Gln Phe Asn Ser Thr Tyr Arg Val Val Ser Val
            290                 295                 300
Leu Thr Val Leu His Gln Asp Trp Leu Asn Gly Lys Glu Tyr Lys Cys
305                 310                 315                 320
Lys Val Ser Asn Lys Gly Leu Pro Ser Ser Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Gln Glu Glu Met Thr Lys Asn Gln Val Ser Leu Thr Cys Leu Val
            355                 360                 365
Lys Gly Phe Tyr Pro Ser Asp Ile Ala Val Glu Trp Glu Ser Asn Gly
            370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Arg Leu Thr Val Asp Lys Ser Arg Trp
                405                 410                 415
Gln Glu Gly Asn Val Phe Ser Cys Ser Val Met His Glu Ala Leu His
            420                 425                 430
```

```
Asn His Tyr Thr Gln Lys Ser Leu Ser Leu Ser Leu Gly
        435                 440                 445
```

IL-17 ANTIBODY FORMULATION AND METHOD OF TREATMENT USING SAME

The present invention relates to the field of medicine. More particularly, the present invention relates to a pharmaceutical formulation of an anti-IL-17 antibody. This anti-IL-17 antibody pharmaceutical formulation is expected to be useful in treating Rheumatoid Arthritis (RA), Psoriasis (Ps), Ankylosing Spondilitis (AS), Psoriatic Arthritis (PA) or Multiple Myeloma (MM).

Pharmaceutical formulations of anti-IL-17 antibodies are needed for the treatment of patients with RA, Ps, AS, PA or MM. Certain concentrations of anti-IL-17 antibodies are needed for pharmaceutical formulations so that the antibody can be delivered subcutaneously to the patient. This pharmaceutical formulation with a certain concentration of the anti-IL-17 antibody must maintain physical and chemical stability of the anti-IL-17 antibody, while also avoiding viscosity that can unacceptably increase delivery time and force needed from a needle or auto-injector device.

Anti-IL-17 antibodies are disclosed in WO 07/70750 that neutralize biological activity associated with human IL-17 (SEQ ID NO: 1). In addition, WO 07/70750 discloses pharmaceutical compositions of anti-IL-17 monoclonal antibodies. With certain formulations for mAb 126, an anti-IL-17 antibody disclosed in WO 07/70750, it was discovered by Applicant as part of the present invention that three stability problems exist at concentrations in solutions greater than or equal to 50 mg/mL: liquid-liquid phase separation; gel formation or solid phase change; and chemical instability. Thus, pharmaceutical formulations for certain concentrations of anti-IL-17 antibodies are needed that avoid these observed problems. A need exists for alternative anti-IL-17 antibody pharmaceutical formulations. Further, a need exists for alternative anti-IL-17 antibody pharmaceutical solution formulations.

Accordingly, the present invention provides a pharmaceutical formulation comprising an anti-IL-17 antibody at a concentration in the range of about 80 mg/mL to about 150 mg/mL, citrate buffer at a concentration of about 20 mM, sodium chloride at a concentration of about 200 mM, polysorbate-80 at a concentration in the range of about 0.02% (w/v) to about 0.03% (w/v), and a pH at about 5.7, wherein the anti-IL-17 antibody comprises an antibody with a light chain (LC) and a heavy chain (HC), wherein said LC is the amino acid sequence of SEQ ID NO: 4 and said HC is the amino acid sequence of SEQ ID NO: 5. The present invention also provides a pharmaceutical formulation comprising an anti-IL-17 antibody at a concentration of about 80 mg/mL, citrate buffer at a concentration of about 20 mM, sodium chloride at a concentration of about 200 mM, polysorbate-80 at a concentration of about 0.03%, and pH at about 5.7, wherein the anti-IL-17 antibody comprises an antibody comprising two light chains (LCs) and two heavy chains (HCs), wherein each LC is the amino acid sequence of SEQ ID NO: 4 and each HC is the amino acid sequence of SEQ ID NO: 5.

In addition, the present invention provides a method of treating RA, Ps, AS, PA or MM comprising administering to a patient in need thereof an effective amount of a pharmaceutical formulation of the present invention. More particularly, the present invention provides a method of treating Ps comprising administering to a patient in need thereof an effective amount of a pharmaceutical formulation of the present invention. Also, the present invention provides a method of treating RA comprising administering to a patient in need thereof an effective amount of a pharmaceutical formulation of the present invention. Also, the present invention provides a method of treating PA comprising administering to a patient in need thereof an effective amount of a pharmaceutical formulation of the present invention. Also, the present invention provides a method of treating AS comprising administering to a patient in need thereof an effective amount of a pharmaceutical formulation of the present invention.

In addition, the present invention provides the pharmaceutical formulation of the present invention for use in therapy. In addition, the present invention provides the pharmaceutical formulation of the present invention for use in the treatment of RA, Ps, AS, PA or MM. More particularly, the present invention provides the pharmaceutical formulation of the present invention for use in the treatment of Ps. Also, the present invention provides the pharmaceutical formulation of the present invention for use in the treatment of RA. Also, the present invention provides the pharmaceutical formulation of the present invention for use in the treatment of PA. Also, the present invention provides the pharmaceutical formulation of the present invention for use in the treatment of AS.

In addition, the present invention provides the use of the pharmaceutical formulation of the present invention in the manufacture of a medicament for the treatment of RA, Ps, AS, PA or MM. More particularly, the present invention provides the use of the pharmaceutical formulation of the present invention in the manufacture of a medicament for the treatment of Ps. Also, the present invention provides the use of the pharmaceutical formulation of the present invention in the manufacture of a medicament for the treatment of RA. Also, the present invention provides the use of the pharmaceutical formulation of the present invention in the manufacture of a medicament for the treatment of PA. Also, the present invention provides the use of the pharmaceutical formulation of the present invention in the manufacture of a medicament for the treatment of AS.

Certain pharmaceutical formulations are preferred. The following enumerated selections describe such preferred classes:

1.) the anti-IL-17 antibody comprises an antibody with an LCVR and an HCVR, wherein said LCVR is the amino acid sequence of SEQ ID NO: 2 and said HCVR is the amino acid sequence of SEQ ID NO: 3; comprises an antibody with a light chain (LC) and a heavy chain (HC), wherein said LC is the amino acid sequence of SEQ ID NO: 4 and said HC is the amino acid sequence of SEQ ID NO: 5; or comprises an antibody comprising two light chains (LCs) and two heavy chains (HCs), wherein each LC is the amino acid sequence of SEQ ID NO: 4 and each HC is the amino acid sequence of SEQ ID NO: 5;

2.) the anti-IL-17 antibody comprises an antibody with a light chain (LC) and a heavy chain (HC), wherein said LC is the amino acid sequence of SEQ ID NO: 4 and said HC is the amino acid sequence of SEQ ID NO: 5;

3.) the anti-IL-17 antibody comprises an antibody comprising two light chains (LCs) and two heavy chains (HCs), wherein each LC is the amino acid sequence of SEQ ID NO: 4 and each HC is the amino acid sequence of SEQ ID NO: 5;

4.) the anti-IL-17 antibody at a concentration in the range of about 80 mg/mL to about 150 mg/mL;

5.) the anti-IL-17 antibody at a concentration of about 80 mg/mL;

6.) the polysorbate-80 at a concentration in the range of about 0.02% (w/v) to about 0.03% (w/v);

7.) the polysorbate-80 at a concentration of about 0.03% (w/v).

Certain pharmaceutical solution formulations are preferred. The following enumerated selections describe such preferred classes:
1.) the anti-IL-17 antibody comprises an antibody with an LCVR and an HCVR, wherein said LCVR is the amino acid sequence of SEQ ID NO: 2 and said HCVR is the amino acid sequence of SEQ ID NO: 3; comprises an antibody with a light chain (LC) and a heavy chain (HC), wherein said LC is the amino acid sequence of SEQ ID NO: 4 and said HC is the amino acid sequence of SEQ ID NO: 5; or comprises an antibody comprising two light chains (LCs) and two heavy chains (HCs), wherein each LC is the amino acid sequence of SEQ ID NO: 4 and each HC is the amino acid sequence of SEQ ID NO: 5;
2.) the anti-IL-17 antibody comprises an antibody with a light chain (LC) and a heavy chain (HC), wherein said LC is the amino acid sequence of SEQ ID NO: 4 and said HC is the amino acid sequence of SEQ ID NO: 5;
3.) the anti-IL-17 antibody comprises an antibody comprising two light chains (LCs) and two heavy chains (HCs), wherein each LC is the amino acid sequence of SEQ ID NO: 4 and each HC is the amino acid sequence of SEQ ID NO: 5;
4.) the anti-IL-17 antibody at a concentration in the range of about 80 mg/mL to about 150 mg/mL;
5.) the anti-IL-17 antibody at a concentration of about 80 mg/mL;
6.) the polysorbate-80 at a concentration in the range of about 0.02% (w/v) to about 0.03% (w/v);
7.) the polysorbate-80 at a concentration of about 0.03% (w/v).

In an embodiment, the present invention also provides a pharmaceutical formulation that comprises a concentration of anti-IL-17 antibody of about 80 mg/mL to about 150 mg/mL. In another embodiment, the present invention provides a pharmaceutical formulation that comprises a concentration of anti-IL-17 antibody in the range of 68 mg/mL to 92 mg/mL. In another embodiment, the present invention provides a pharmaceutical formulation that comprises a concentration of anti-IL-17 antibody of about 80 mg/mL. In another embodiment, the present invention provides a pharmaceutical formulation that comprises a concentration of anti-IL-17 antibody of about 120 mg/mL. In another embodiment, the present invention provides a pharmaceutical formulation that comprises a concentration of anti-IL-17 antibody of about 150 mg/mL.

In an embodiment, the present invention also provides a pharmaceutical formulation that is buffered with citrate buffer in the range of about 15 mM to about 25 mM. In another embodiment, the present invention provides a pharmaceutical formulation that is buffered with citrate buffer in the range of 15 mM to 25 mM. In another embodiment, the present invention provides a pharmaceutical formulation that is buffered with citrate buffer at a concentration of about 15 mM, about 20 mM, about 25 mM, or about 30 mM. In a further embodiment, the present invention provides a pharmaceutical formulation that is buffered with citrate buffer at a concentration of about 20 mM.

In an embodiment, the present invention also provides a pharmaceutical formulation that comprises a concentration of NaCl of about 200 mM to about 300 mM. In another embodiment, the present invention provides a pharmaceutical formulation that comprises a concentration of NaCl of 175 mM to 225 mM. In another embodiment, the present invention provides a pharmaceutical formulation that comprises a concentration of NaCl of about 200 mM, about 250 mM, or about 300 mM. In a further embodiment, the present invention provides a pharmaceutical formulation that comprises a concentration of NaCl of about 200 mM.

In an embodiment, the present invention also provides a pharmaceutical formulation that comprises a concentration of polysorbate-80 or polysorbate-20 of about 0.01% to about 0.04%. In another embodiment, the present invention provides a pharmaceutical formulation that comprises a concentration of polysorbate-80 or polysorbate-20 of 0.02% to 0.04%. In another embodiment, the present invention provides a pharmaceutical formulation that comprises a concentration of polysorbate-80 or polysorbate-20 of about 0.01%, about 0.02%, about 0.03%, or about 0.04%. In a further embodiment, the present invention provides a pharmaceutical formulation that comprises a concentration of polysorbate-80 or polysorbate-20 of about 0.03%.

In an embodiment, the present invention also provides a pharmaceutical formulation that comprises a pH range of about 5.4 to about 6.0. In another embodiment, the present invention provides a pharmaceutical formulation that comprises a pH in the range of 5.4 to 6.0. In another embodiment, the present invention provides a pharmaceutical formulation that comprises a pH of about 5.4, about 5.7, or about 6.0. In a further embodiment, the present invention provides a pharmaceutical formulation that comprises a pH of about 5.7.

The pharmaceutical formulations of the present invention comprise citrate buffer. Citrate buffer can be made with citric acid, trisodium citrate dihydrate, and citric acid monohydrate; or citric acid monohydrate, sodium phosphate dibasic, and citric acid. Also, citrate buffer can be made comprising sodium citrate monobasic, citric acid trisodium salt, or sodium citrate tribasic hydrate. Preferably, citrate buffer is made with sodium citrate dihydrate and citric acid.

The mAb 126 antibody is an anti-IL-17 antibody that consists of two light chains (LCs) and two heavy chains (HCs), wherein each LC is the amino acid sequence of SEQ ID NO: 4 and each HC is the amino acid sequence of SEQ ID NO: 5, and wherein the HCs are cross-linked by disulfide bonds.

The general structure of an "antibody" is very well-known in the art. For an antibody of the IgG type, there are four amino acid chains (two "heavy" chains and two "light" chains) that are cross-linked via intra- and inter-chain disulfide bonds. When expressed in certain biological systems, antibodies having unmodified human Fc sequences are glycosylated in the Fc region. Antibodies may be glycosylated at other positions as well. One of skill in the art will appreciate that antibodies for use in the formulation of the present invention may contain such glycosylation. The subunit structures and three-dimensional configurations of antibodies are well known in the art. Each heavy chain is comprised of an N-terminal heavy chain variable region ("HCVR") and a heavy chain constant region ("HCCR"). The heavy chain constant region is comprised of three domains (CH1, CH2, and CH3) for IgG, IgD, and IgA; and 4 domains (CH1, CH2, CH3, and CH4) for IgM and IgE. Each light chain is comprised of a light chain variable region ("LCVR") and a light chain constant region ("LCCR"). The variable regions of each light/heavy chain pair form the antibody binding site.

An anti-IL-17 antibody for use in the formulations of the present invention can be produced using techniques well known in the art, e.g., recombinant technologies, phage display technologies, synthetic technologies, or combinations of such technologies or other technologies readily known in the art. Methods for producing and purifying antibodies and antigen-binding fragments are well known in the art and can be found, for example, in Harlow and Lane (1988) *Antibodies, A*

*Laboratory Manual*, Cold Spring Harbor Laboratory Press, Cold Spring Harbor, New York, chapters 5-8 and 15, ISBN 0-87969-314-2.

An anti-IL-17 antibody for use in the formulations of the present invention is an engineered antibody that has been designed to have frameworks, hinge regions, and constant regions of human origin that are identical with or substantially identical (substantially human) with frameworks and constant regions derived from human genomic sequences. Fully human frameworks, hinge regions, and constant regions are those human germline sequences as well as sequences with naturally-occurring somatic mutations and/or those with engineered mutations. An antibody for use in a formulation of the present invention may comprise framework, hinge, or constant regions derived from a fully human framework, hinge, or constant region containing one or more amino acid substitutions, deletions, or additions therein. Further, an antibody for use in a formulation of the present invention is substantially non-immunogenic in humans.

Stability of an antibody in solution depends on the chemical stability and physical stability of the antibody in the formulation in which the antibody is solubilized. Oxidation, deamidation, and hydrolysis are examples of chemical stability issues that an antibody can have in a formulation. Aggregation and gel formation are examples of physical stability issues that an antibody can have in a formulation. Another physical stability issue with antibodies in a solution formulation may be liquid-liquid phase separation (LLPS); LLPS in an antibody solution typically first appears as opalescence, followed by separation into light and heavy phases. Cloud point is the temperature where LLPS is first observed for a given condition; cloud point measures the temperature where solutions become white opaque as a result of the formation of micro-phases which ultimately resolve into the heavy and light phases traditionally associated with phase separation.

A pharmaceutical formulation is a stable formulation wherein the degree of degradation, modification, aggregation, loss of biological activity and the like, of proteins/antibodies therein is acceptably controlled, and does not increase unacceptably with time. Stability may be assessed by methods well-known in the art, including measurement of a sample's light scattering, apparent attenuation of light (absorbance, or optical density), size (e.g. by size exclusion chromatography (SEC)), in vitro or in vivo biological activity and/or properties measured by differential scanning calorimetry (DSC). Other methods for assessing stability are well known in the art and can also be used according to the present invention. As measured by SEC, the % monomer for an anti-IL-17 pharmaceutical formulation should be greater than 90% after storage at 5° C. for a period of 3 months, 6 months, 9 months, 12 months, 18 months, or preferably 2 years. As measured by cation exchange chromatography (CEX), the percent total acid variants should not exceed 30% for an anti-IL-17 pharmaceutical formulation after storage at 5° C. for a period of 3 months, 6 months, 9 months, 12 months, 18 months, or preferably 2 years. For measurements of purity by reduced CE-SDS, an anti-IL-17 pharmaceutical formulation should have a purity greater than 85% after storage at 5° C. for a period of 3 months, 6 months, 9 months, 12 months, 18 months, or preferably 2 years. Preferably, an anti-IL-17 antibody pharmaceutical formulation meets one of the aforementioned standards for stability at a temperature of 5° C. for a solution stored for two years. More preferably, an anti-IL-17 antibody pharmaceutical formulation meets all the aforementioned standards for stability at a temperature of 5° C. for a solution stored for two years.

The pharmaceutical formulations of the present invention can be in the liquid dosage form of a solution, emulsion, or suspension. Preferably, the pharmaceutical formulations of the present invention are in the liquid dosage form of a solution.

Administration of the pharmaceutical formulations of the present invention may be via parenteral administration. Parenteral administration is commonly understood in the medical literature as the injection of a dosage form into the body by a sterile syringe or some other mechanical device such as an infusion pump. Parenteral routes can include intravenous, intramuscular, subcutaneous, and intraperitoneal routes of administration. Subcutaneous administration is a preferred route.

The pharmaceutical formulations of the present invention can be used to treat subjects with RA, Ps, AS, PA or MM. An effective amount of the anti-IL-17 antibody formulation of the present invention is the quantity which delivers an amount of the anti-IL-17 antibody that results in a desired therapeutic and/or prophylactic effect without causing unacceptable side-effects when administered to a subject with increased IL-17 levels.

EXAMPLE 1

Formulating mAb 126

TABLE 1 mAb 126 Drug Product Formulation

| Component | Concentration (mg/mL) |
| --- | --- |
| mAb 126 | 80 |
| Sodium Citrate Dihydrate | 5.106 |
| Citric Acid Anhydrous | 0.507 |
| Sodium Chloride | 11.69 |
| Polysorbate 80 | 0.30 |
| Water for Injection | q.s. to 1 mL |
| Hydrochloric Acid | pH adjustment |
| Sodium Hydroxide | pH adjustment |

TABLE 2

Buffer Excipient Composition

| Component | mg/mL |
| --- | --- |
| Sodium Citrate Dihydrate | 5.106 |
| Citric Acid Anhydrous | 0.507 |
| Sodium Chloride | 11.69 |
| Polysorbate 80 | 0.414 |

The manufacturing process for the anti-IL-17 antibody pharmaceutical solution formulation for mAb 126 (Table 1) consists of first compounding of the buffer excipient composition (Table 2), followed by compounding of the final drug product formulation.

The buffer excipient composition (Table 2) is prepared, filtered, and stored for drug product formulation compounding. An appropriate quantity of water at a temperature of 20+/−5° C. is weighed into a tared empty vessel of appropriate size. The appropriate quantity of sodium citrate is added and mixed; the appropriate quantity of citric acid is then added and mixed. Then, the appropriate quantity of sodium chloride is added and mixed. Polysorbate 80 is accurately weighed out in a glass container and an appropriate quantity of water at a temperature of 20+/−5° C. is added into the glass container to give the concentration in Table 2, and the solution is mixed. The entire content of the polysorbate 80 solution is added to the other excipients. The polysorbate 80 solution container is rinsed with water to ensure the entire content is transferred. After addition of the polysorbate 80 solution, the solution is mixed. After dissolution and mixing has been completed, the pH of the solution is checked to be within 5.7+/−0.2; adjustment with HCl or NaOH solution is done if necessary. The buffer excipient composition is passed through a filter (polyvinylidene fluoride [PVDF]) for bioburden reduction.

The buffer excipient composition is supplemented with additional polysorbate 80 to account for the lower concentration (0.2 mg/mL polysorbate-80) in the active pharmaceutical ingredient (API) compared to the final drug product formulation. Since the concentration of mAb 126 in the API will vary, the amount of buffer needed for dilution will also change. This variation requires that the concentration of polysorbate 80 be adjusted for the buffer excipient composition recipe with each batch.

The stored mAb 126 API containers (mAb 126 is expressed in cells, purified, and concentrated; the resulting API is then frozen at about 150 mg/mL to about 160 mg/mL mAb 126 in 20 mM citrate buffer, 200 mM NaCl, 0.02% polysorbate-80, at pH about 5.7) are equilibrated to a temperature of 20+/−5° C. The API solution is then mixed with an appropriate amount of the buffer excipient solution to achieve 80% of the theoretical batch size. The pH of the solution is checked to be within 5.7+/−0.2. After pH adjustment, the solution is mixed and a sample is taken for an in-process UV assay to determine the mAb 126 concentration. An appropriate quantity of the buffer excipient solution is added to reach the final target batch weight. After mixing, the pH of the solution is checked to be within 5.7+/−0.2, and the osmolality of the solution is checked to be within 360-480 mOsm/Kg. The mAb 126 drug product solution is passed through a PVDF filter for bioburden reduction and stored at 5° C.

EXAMPLE 2

Phase Separation mAb 126 is found to have a propensity to phase separate while in solutions that are below 0° C. Liquid-liquid phase separation (LLPS) needs to be solved since storage of the mAb 126 drug product will be at 5° C. Storage of drug product at 5° C. requires stability for periodic refrigerator temperature excursions below 0° C. Increasing the NaCl concentration is shown to lower the temperature at which LLPS occurs in mAb 126 formulations, and increasing the citrate concentration is also shown to lower the temperature at which LLPS occurs in mAb 126 formulations.

LLPS events are tested based on a technique developed specifically for the temperature range (phase separation occurring between −12 and 0° C.) encountered for mAb 126. Two milliliter (mL) samples of 10 to 200 mg/mL mAb 126 were placed in a LyoStar II (FTS Systems) lyophilization unit with the cycle shown in Table 3. Pressure was kept at atmospheric for the experiments. Sample conditions are tested at least three times and the standard deviation is approximately 0.5° C. for samples measured in triplicate. The samples are visually monitored during the lyophilization cycle for signs of phase separation, including cloud point (white opaque appearance) and the formation of a dense, protein rich layer at the bottom of the vial. Samples appear increasingly opalescent during cooling, but this effect is easily differentiable from cloud point. When cloud point occurs, the sample becomes an opaque white solution in less than a second versus a gradual increased opalescence where an object behind a vial is still visible through the sample.

TABLE 3

| Lyophilization Cycle for Liquid-Liquid Phase Separation Testing | | | |
|---|---|---|---|
| Step | 1 | 2 | 3 |
| Cooling Rate (° C./min) | 5 | 1 | 5 |
| Target (° C.) | 5 | −30 | 20 |
| Hold Time (min) | 10 | 20 | >20 |

As shown in Table 4, increasing the NaCl concentration is shown to depress the cloud point temperature. The factors which limit increasing the NaCl concentration in the anti-IL-17 antibody pharmaceutical formulation are hyper-tonicity and other non-phase-separation effects; 200 mM NaCl avoids these problems while still depressing the cloud point temperature. Also, LLPS in mAb126 is shown to be bimodal at all NaCl concentrations, except 300 mM NaCl; LLPS is strongest at a concentration of 100 mg/mL mAb 126, and the phase separation effects lessen as the concentration moves higher or lower than 100 mg/mL.

TABLE 4

| Liquid-Liquid Phase Separation: NaCl and mAb 126 Concentration Effects (Cloud Point ° C.) | | | | | |
|---|---|---|---|---|---|
| mAb 126 Conc. (mg/mL) | 10 | 50 | 100 | 150 | 200 |
| 50 mM NaCl | −4.1 | 2.1 | 5 | | |
| 100 mM NaCl | | −1.2 | 2.7 | 1.1 | |
| 150 mM NaCl | | −7.5 | −4 | −5.7 | −10.4 |
| 200 mM NaCl | | −8.5 | −7 | −10.2 | −10.8 |
| 250 mM NaCl | | | −6.8 | −11.3 | |
| 300 mM NaCl | | −12.5 | −9.9 | −12.4 | −8.8 |

The effect of pH on cloud point of a mAb 126 solution is measured. The cloud point was found to be minimized at two pHs, pH 4 and pH6. pH 6 should be considered optimal over pH 4 when selecting a formulation for mAb 126, because chemical instability of mAb 126 at pH 4 precludes using the low cloud point at pH 4. Given the gel formation at pH 6.3-6.4, shown in Example 3, for the mAb 126 pharmaceutical formulations, pH 5.7+/−0.3 is preferred over pH 6+/−0.3 in order to allow for a pH range that remains stable over the shelf-life of the pharmaceutical formulation.

Effects of various commonly used buffers on liquid-liquid phase separation are explored to understand what the optimal buffer system would be for mAb 126 (Table 5); citrate buffer is found to be most effective at reducing the temperature at which LLPS occurs. These studies are conducted with 150 mM NaCl. Acetate buffer is comparable to citrate buffer at pH 5 in terms of the effect on cloud point; however, chemical instability at pH 5 makes this pH condition less favorable.

The concentration of citrate is shown to positively affect LLPS (Table 6). While citrate depresses cloud point up to 50 mM; citrate buffer is also reported to cause more pain on injection. As such, citrate concentrations higher than 30 mM are likely to be unacceptable from a patient compliance standpoint.

TABLE 5

Buffer Effects on Cloud Point Temperature
with 150 mg/mL mAb 126

| Buffer | mM | pH | Cloud Point (° C.) |
|---|---|---|---|
| Acetate | 10 | 5 | −4.1 |
| Citrate | 10 | 5 | −4.4 |
| Histidine | 10 | 6 | −2.2 |
| Citrate | 10 | 6 | −8.1 |

TABLE 6

Liquid-Liquid Phase Separation: Citrate Concentration
Effects with 150 mg/mL mAb 126

| Citrate conc. | Cloud Point (° C.) |
|---|---|
| 5 mM | −6.3 |
| 10 mM | −8.2 |
| 20 mM | −10.2 |
| 30 mM | −13.6 |
| 40 mM | −14.6 |

EXAMPLE 3

Gel Formation

Biologic drug products are stored at 5° C.+/−3° C. to minimize chemical and physical degradation over the shelf-life of a product. Events such as thermodynamic solid phase change or gel formation are typically not acceptable, even if reversible, because they can negatively affect stability and hinder the required visual inspection of samples prior to use.

Solid phase change is observed in high concentration samples of mAb 126 at pH conditions <pH 5 and >pH 7 at 5° C. This thermodynamic event is shown to be reversible by equilibrating the vials at room temperature. Consequently, samples are tested at various pH conditions and monitored for thermodynamic changes in order to find the phase boundaries more precisely. These tests are conducted by dialyzing samples into pH 7, citrate buffer at 5° C. to induce phase change. The solid material is then dialyzed at the same temperature into conditions of interest to ascertain if samples would reverse to the solution state. Equilibrium testing method is preferable to long-term sample storage with intermittent inspections because, while a particular formulation may be thermodynamically unstable, the kinetics of solid phase change may require months to occur in some cases.

Studies are conducted with 100 mg/mL or 150 mg/mL mAb 126 at 200 mM NaCl, 10 mM citrate buffer in 0.1 pH increments to find where the boundaries are for solid phase formation. The transition between phases is found between pH 6.3 and 6.4 at 5° C. Because of the phase boundary, the target pH for a mAb 126 formulation is lowered from pH 6 to 5.7 to ensure a stable storage window.

Two experiments with 80 mg/mL mAb 126 at 5° C. are carried out in 20 mM citrate buffer, 200 mM NaCl, and 0.03% polysorbate-80; there is no gel formation at or below pH 6.1, while gel formation occurs above pH 6.1. These experiments indicate that the formulation with 80 mg/mL mAb 126 has a window from pH 5.7+/−0.3 pH units wide that avoids gel formation.

EXAMPLE 4

Chemical Instability

For a pharmaceutical formulation to achieve stability, both physical and chemical sources of instability need to be addressed in the formulation. Chemical instability can result in degradation of the antibody.

In order to assess the effect of pH on chemical stability of mAb 126 at 100 and 150 mg/mL, samples of mAb 126 are analyzed for increases in total % acid variants by chromatography. The range of pH 4 to 7 is explored in half pH unit increments. The buffer for the study includes 10 mM citrate buffer, 150 mM NaCl and 0.02% polysorbate 80. Two mL solutions are stored in 3 mL glass vials with serum stoppers. Samples in these pH environments are stored at 5° C., 25° C., and 40° C. in order to more accurately model the temperature effect on the different forms of degradation. Samples are analyzed using Cation Exchange (CEX) HPLC using UV detector and a Dionex ProPac WCX-10 column (4×250 mm) using pH 6 10 mM Bis Tris Propane (Mobile Phase A) and pH 9.6 10 mM Bis Tris Propane, 50 mM NaCl (Mobile phase B).

By CEX, increases in total % acid variants (%AV) are the more reliable indicator of degradation for mAb 126. Vials of mAb 126 stored at 25° C. are shown by CEX to be most stable between pH 5-6 and least stable at more alkaline pH conditions. When samples are stored at 40° C., pH 5 and 5.5 are the most stable, with pH 6 appearing only slightly more stable than the higher pH environments. These results show that the pH of the pharmaceutical solution formulation for mAb 126 should be between pH 5 and pH 6.

EXAMPLE 5

Design of Experiment (DOE) Study

The DOE study uses a multivariate approach to examine the physical and chemical stability of mAb 126 solution formulations. mAb 126 solution formulations are prepared according to Table 7. Each variable is explored at five levels to measure any curvature which might exist in the output response parameters or interactions between the input variables. The center point condition for the experiment is 20 mM citrate, 200 mM NaCl, pH 5.7, 0.02% polysorbate 80. Three center points are dispersed throughout the design. Independently preparing three center points provides an estimation of certainty in the analytical data without requiring all of the conditions to be prepared and analyzed in duplicate or triplicate. Samples are stored at four temperature conditions (5, 25, 30 and 40° C.). This range of temperatures allows for estimations of the activation energies for the results. Additionally, higher temperature storage enables earlier predictions of optimal formulation conditions.

A number of analytical techniques are selected to monitor chemical and physical stability including size exclusion chromatography (SEC), cation exchange chromatography (CEX) HPLC, HIAC-based particle analysis, digital-image based particle analysis by micro-flow imaging (MFI, Protein Simple/Brightwell Model DPA 4200 with size range of 2-100 um), visual appearance, reduced and non-reduced Bioanalyzer Lab-on-a-Chip (LoC), pH, viscosity, and UV absorption (to measure protein content).

Using the data from all temperatures from the initial three month period, activation energies (Ea) are calculated employing an Arrhenius kinetic model (zero or first Order). Energies are found using non-linear regression of all Runs. The model is then employed to extrapolate trends out to 24 months at the relevant commercial storage temperature (5° C.). Zero order Arrhenius modeling is used for SEC (monomer, polymer Rel.

Sub/Impurities), CEX (acid variants), reduced/non-reduced LoC, and UV content. The best fit for CEX basic variant trends is a first order model.

TABLE 7

Experimental Design

| Run | pH | [PS80] | [NaCl] | [mAb 126] | [Buffer] | Buffer Type |
|---|---|---|---|---|---|---|
| 1 | 5.7 | 0.02 | 200 | 120 | 20 | Citrate |
| 2 | 6 | 0.01 | 150 | 105 | 25 | Citrate |
| 3 | 6 | 0.03 | 150 | 105 | 15 | Citrate |
| 4 | 5.7 | 0 | 200 | 120 | 20 | Citrate |
| 5 | 5.4 | 0.03 | 150 | 135 | 15 | Citrate |
| 6 | 6 | 0.01 | 250 | 105 | 15 | Citrate |
| 7 | 5.7 | 0.02 | 200 | 90 | 20 | Citrate |
| 8 | 5.7 | 0.02 | 100 | 120 | 20 | Citrate |
| 9 | 6.3 | 0.02 | 200 | 120 | 20 | Citrate |
| 10 | 5.1 | 0.02 | 200 | 120 | 20 | Citrate |
| 11 | 6 | 0.03 | 250 | 105 | 25 | Citrate |
| 12 | 5.4 | 0.01 | 150 | 105 | 15 | Citrate |
| 13 | 5.4 | 0.03 | 250 | 135 | 25 | Citrate |
| 14 | 6 | 0.03 | 150 | 135 | 25 | Citrate |
| 15 | 5.7 | 0.02 | 200 | 120 | 20 | Citrate |
| 16 | 5.7 | 0.02 | 200 | 120 | 10 | Citrate |
| 17 | 5.4 | 0.01 | 250 | 135 | 15 | Citrate |
| 18 | 5.4 | 0.01 | 150 | 135 | 25 | Citrate |
| 19 | 6 | 0.03 | 250 | 135 | 15 | Citrate |
| 20 | 5.7 | 0.04 | 200 | 120 | 20 | Citrate |
| 21 | 5.4 | 0.03 | 250 | 105 | 15 | Citrate |
| 22 | 6 | 0.01 | 150 | 135 | 15 | Citrate |
| 23 | 5.4 | 0.03 | 150 | 105 | 25 | Citrate |
| 24 | 5.7 | 0.02 | 300 | 120 | 20 | Citrate |
| 25 | 5.7 | 0.02 | 200 | 150 | 20 | Citrate |
| 26 | 6 | 0.01 | 250 | 135 | 25 | Citrate |
| 27 | 5.4 | 0.01 | 250 | 105 | 25 | Citrate |
| 28 | 5.7 | 0.02 | 200 | 120 | 30 | Citrate |
| 29 | 5.7 | 0.02 | 200 | 120 | 20 | Citrate |

Size Exclusion Chromatography

The two variables with the strongest effect on percent monomer based on SEC results are pH and mAb 126 concentration. The effect of mAb 126 concentration is linear with increasing protein concentration resulting in decreased monomer purity.

Three input variables (pH, NaCl concentration, and buffer concentration) show curvature in their effect on percent monomer. With respect to NaCl and citrate concentration, values near the center point are the most stable. Lower pH conditions are slightly more stable than the center point, but other degradation pathway results make lowering the target pH less attractive.

Interactions between the effect of pH and protein concentration occur with the effects of protein concentration being reduced at pH conditions below 5.7. The two year prediction for monomer purity at the center point conditions of the study is slightly below 96.7%. Polysorbate 80 concentration has little effect on stability from 0.02-0.04%.

Cation Exchange Chromatography

The CEX analysis focuses on the growth of acidic species over time. Statistical modeling of CEX %AV (Ea is 23.7 kcal/g-mol) shows that little chemical modification should be expected after 24 months of storage at 5° C. Acidic variant generation is minimized near the center point for pH, but increases with greater citrate concentration. mAb 126 and Polysorbate 80 concentration trends suggest that the center point is close to the least optimal position; however, based on the magnitude of the y-axis scale, the difference in center point stability to other conditions is essentially negligible.

Reduced Bioanalyzer LoC

Reduced LoC percent purity is a combination of the relative percentages of heavy and light chains. The two input variables with the strongest influence on the 24-month predictions are pH and NaCl concentration. Percent purity is maximized near the center point of 200 mM NaCl. The percent purity increases with increasing pH. Even at the extreme formulation conditions tested in the DOE study, the molecule is still >98% pure, indicating that the antibody is stable as measured by reduced LoC over the range of the multivariate analysis. The Ea is 21.8 kcal/g-mol.

Combined Projections

All conditions in the design space studied during this experiment have 2 year shelf life projections that predict <5% degradation. However, other physical factors preclude pH conditions above pH 6.3; therefore, the target conditions for the formulation should not be near this pH edge. Additionally, it is important to select a target that is in an optimal global maximum for the input variables explored. Based on manufacturing considerations, which indicate that >0.01% polysorbate 80 is needed for pumping, the polysorbate 80 target is 0.03%. Based on the results of this study, the optimal formulation conditions is 20 mM citrate, 200 mM NaCl, pH 5.7 with 0.03% polysorbate 80.

EXAMPLE 6

Stability at 80 mg/mL mAb 126

The stability of 80 mg/mL mAb 126 in 20 mM citrate, 200 mM NaCl, pH 5.7 with 0.03% polysorbate 80 is tested out to 24 months. For storage at 5° C., stability of the anti-IL-17 antibody pharmaceutical formulation is measured at 0, 1, 3, 6, 9, 12, 18, and 24 months. 5° C. will be the expected storage temperature for the anti-IL-17 antibody pharmaceutical formulation. Accelerated stability studies at 25° C. are run for 1, 3, and 6 months.

A number of analytical techniques are selected to monitor chemical and physical stability including size exclusion chromatography HPLC, cation exchange chromatography HPLC, visual appearance, pH, and UV absorption. CE-SDS is performed utilizing the Beckman Coulter IgG Purity/Heterogeneity kit with a Beckman Coulter ProteomeLab PA800 Enhanced or Plus capillary electrophoresis (CE) instrument. For Reduced CE-SDS, samples are analyzed in a bare-fused silica capillary under denatured, reducing conditions by molecular sieving through a replaceable gel polymer matrix after each sample injection. For non-reduced CE-SDS, samples are diluted to approximately 5 mg/mL in water and subsequently diluted in sample diluent (20 mM IAM in 100 mM Tris, 1% SDS, pH 9.0) to approximately 1 mg/mL. Afterwards samples are analyzed in a bare-fused silica capillary under denatured, non-reducing conditions by molecular sieving through a replaceable gel polymer matrix at constant voltage. For both methods, UV detection is performed at 214 nm. Results are shown in Table 8.

TABLE 8

Stability Data for mAb 126 at 80 mg/mL

| Analytical Property | Storage Condition | Month | | | |
|---|---|---|---|---|---|
| | | 0 | 1 | 3 | 6 | 9 |
| Potency (Bioassay), % | 5° C. | 87 | — | — | — | 108 |
| | 25° C./60% RH | | 106 | — | 109 | — |
| Quantity (UV), mg/mL | 5° C. | 75.4 | — | 76.2 | 75.5 | 75.4 |
| | 25° C./60% RH | | 75.3 | 76.0 | 76.5 | — |

TABLE 8-continued

Stability Data for mAb 126 at 80 mg/mL

| Analytical Property | Storage Condition | Month 0 | 1 | 3 | 6 | 9 |
|---|---|---|---|---|---|---|
| Monomer Purity (SEC), % | 5° C. | 98.3 | — | 98.1 | 98.3 | 97.9 |
|  | 25° C./60% RH |  | 98.3 | 97.6 | 97.6 | — |
| Rel Subs/Impurities: Total (SEC), % | 5° C. | 1.7 | — | 1.9 | 1.7 | 2.1 |
|  | 25° C./60% RH |  | 1.7 | 2.4 | 2.4 | — |
| mAb 126 Purity (CE-SDS, Reduced), % | 5° C. | 97.8 | — | 97.4 | 97.3 | 97.2 |
|  | 25° C./60% RH |  | 97.4 | 96.9 | 96.3 | — |
| Charge Heterogeneity (CEX) [Main Peak], % | 5° C. | 53.9 | — | 53.0 | 54.1 | 55.1 |
|  | 25° C./60% RH |  | 56.7 | 59.7 | 60.0 | — |
| Charge Heterogeneity (CEX) [Acidic Variants], % | 5° C. | 13.4 | — | 15.4 | 15.3 | 16 |
|  | 25° C./60% RH |  | 15.8 | 21.4 | 27.4 | — |
| Charge Heterogeneity (CEX) [Basic Variants], % | 5° C. | 32.8 | — | 31.6 | 30.7 | 28.9 |
|  | 25° C./60% RH |  | 27.5 | 18.8 | 13.0 | — |
| pH | 5° C. | 5.7 | — | 5.7 | 5.7 | 5.7 |
|  | 25° C./60% RH |  | 5.7 | 5.7 | 5.7 | — |
| Physical Appearance | 5° C. | NT | Pass[1] | — | — | Pass |
|  | 25° C./60% RH |  | NT | — | — | — |
| Particulate Matter (greater than or equal to 10 micrometer), particles per container | 5° C. | 289 | — | 131 | 184 | 63 |
|  | 25° C./60% RH |  | 194 | 177 | 369 | — |
| Particulate Matter (greater than or equal to 25 micrometer), particles per container | 5° C. | 9 | — | 8 | 31 | 3 |
|  | 25° C./60% RH |  | 4 | 60 | 20 | — |

[1]Physical appearance was not performed at lot release or the 1 month time point. Result shown was obtained after storage at 5° C. for approximately 2.5 months.

Sequence Listing (human IL-17)

SEQ ID NO: 1
MTPGKTSLVS LLLLLSLEAI VKAGITIPRN PGCPNSEDKN
FPRTVMVNLN IHNRNTNTNP KRSSDYYNRS TSPWNLHRNE
DPERYPSVIW EAKCRHLGCI NADGNVDYHM NSVPIQQEIL
VLRREPPHCP NSFRLEKILV SVGCTCVTPI VHHVA (LCVR)

SEQ ID NO: 2
DIVMTQTPLS LSVTPGQPAS ISCRSSRSLV HSRGNTYLHW
YLQKPGQSPQ LLIYKVSNRF IGVPDRFSGS GSGTDFTLKI
SRVEAEDVGV YYCSQSTHLP FTFGQGTKLE IK (HCVR)

SEQ ID NO: 3
QVQLVQSGAE VKKPGSSVKV SCKASGYSFT DYHIHWVRQA
PGQGLEWMGV INPMYGTTDY NQRFKGRVTI TADESTSTAY
MELSSLRSED TAVYYCARYD YFTGTGVYWG QGTLVTVSS (Light chain)

SEQ ID NO: 4
DIVMTQTPLS LSVTPGQPAS ISCRSSRSLV HSRGNTYLHW
YLQKPGQSPQ LLIYKVSNRF IGVPDRFSGS GSGTDFTLKI
SRVEAEDVGV YYCSQSTHLP FTFGQGTKLE IKRTVAAPSV
FIFPPSDEQL KSGTASVVCL LNNFYPREAK VQWKVDNALQ
SGNSQESVTE QDSKDSTYSL SSTLTLSKAD YEKHKVYACE
VTHQGLSSPV TKSFNRGEC (Heavy chain)

SEQ ID NO: 5
QVQLVQSGAE VKKPGSSVKV SCKASGYSFT DYHIHWVRQA
PGQGLEWMGV INPMYGTTDY NQRFKGRVTI TADESTSTAY
MELSSLRSED TAVYYCARYD YFTGTGVYWG QGTLVTVSSA
STKGPSVFPL APCSRSTSES TAALGCLVKD YFPEPVTVSW
NSGALTSGVH TFPAVLQSSG LYSLSSVVTV PSSSLGTKTY
TCNVDHKPSN TKVDKRVESK YGPPCPPCPA PEFLGGPSVF
LFPPKPKDTL MISRTPEVTC VVVDVSQEDP EVQFNWYVDG
VEVHNAKTKP REEQFNSTYR VVSVLTVLHQ DWLNGKEYKC
KVSNKGLPSS IEKTISKAKG QPREPQVYTL PPSQEEMTKN
QVSLTCLVKG FYPSDIAVEW ESNGQPENNY KTTPPVLDSD
GSFFLYSRLT VDKSRWQEGN VFSCSVMHEA LHNHYTQKSL
SLSLG

We claim:

1. A pharmaceutical formulation comprising an anti-IL-17 antibody at a concentration in the range of about 80 mg/ml to about 150 mg/ml, citrate buffer at a concentration of about 20 mM, sodium chloride at a concentration of about 200 mM, polysorbate-80 at a concentration in the range of about 0.02% (w/v) to about 0.03% (w/v), and pH at about 5.7, wherein the anti-IL-17 antibody comprises a light chain given by the amino acid sequence of SEQ ID NO:4, and a heavy chain given by the amino acid sequence of SEQ ID NO: 5.

2. The formulation of claim 1, wherein the concentration of the anti-IL-17 antibody is about 80 mg/ml.

3. The formulation of claim 2, wherein the formulation is an anti-IL-17 antibody pharmaceutical solution formulation.

4. A pharmaceutical formulation comprising an anti-IL-17 antibody at a concentration of about 80 mg/ml, citrate buffer at a concentration of about 20 mM, sodium chloride at a concentration of about 200 mM, polysorbate-80 at a concentration of about 0.03%, and pH at about 5.7, wherein the anti-IL-17 antibody comprises an antibody comprising two light chains (LCs), each given by the amino acid sequence of SEQ ID NO: 4, and two heavy chains (HCs), each given by the amino acid sequence of SEQ ID NO: 5.

5. A pharmaceutical solution formulation comprising an anti-IL-17 antibody at a concentration of about 80 mg/ml, citrate buffer at a concentration of about 20 mM, sodium chloride at a concentration of about 200 mM, polysorbate-80 at a concentration of about 0.03%, and pH at about 5.7, wherein the anti-IL-17 antibody comprises an antibody comprising two light chains (LCs), each given by the amino acid sequence of SEQ ID NO: 4, and two heavy chains (HCs), each given by the amino acid sequence of SEQ ID NO: 5.

6. A method of treating rheumatoid arthritis, psoriasis, ankylosing spondilitis, psoriatic arthritis or multiple myeloma comprising administering to a patient in need thereof an effective amount of the pharmaceutical formulation of claim 1.

7. A method of treating rheumatoid arthritis, psoriasis, ankylosing spondilitis, psoriatic arthritis or multiple myeloma comprising administering to a patient in need thereof an effective amount of the pharmaceutical formulation of claim 4.

8. A method of treating rheumatoid arthritis, psoriasis, ankylosing spondilitis, psoriatic arthritis or multiple myeloma comprising administering to a patient in need thereof an effective amount of the pharmaceutical solution formulation of claim 5.

* * * * *